United States Patent [19]

Angelchik

[11] Patent Number: 5,624,432
[45] Date of Patent: Apr. 29, 1997

[54] ILLUMINATING BOUGIE AND METHODS FOR DIAGNOSTIC, THERAPEUTIC AND SURGICAL PROCEDURES

[76] Inventor: Jean P. Angelchik, 522 W. Northview, Phoenix, Ariz. 85012

[21] Appl. No.: 390,624

[22] Filed: Feb. 17, 1995

Related U.S. Application Data

[63] Continuation of Ser. No. 131,995, Oct. 4, 1993, abandoned, which is a continuation-in-part of Ser. No. 73,172, filed as PCT/US92/07356, Aug. 26, 1992, abandoned, which is a continuation-in-part of Ser. No. 772,332, Oct. 7, 1991, abandoned.

[51] Int. Cl.$^6$ .................................................. A61B 17/36
[52] U.S. Cl. ........................... 606/2; 606/15; 607/89
[58] Field of Search ............................. 128/665; 607/88, 607/89, 92, 93; 606/2, 10, 11, 12

[56] References Cited

U.S. PATENT DOCUMENTS

| | | | |
|---|---|---|---|
| 4,336,809 | 6/1982 | Clark | 128/665 |
| 4,660,925 | 4/1987 | McCaughan, Jr. | 606/15 |
| 5,054,867 | 10/1991 | Wagnieres et al. | 128/665 |
| 5,074,632 | 12/1991 | Potter . | |

OTHER PUBLICATIONS

V. Russo "*Fibers In Medicine*" Isituto Ricorca Onde Electromagnetiche, C.N.R.—Firenze, pp. 247–271.

*Primary Examiner*—Stephen C. Pellegrino
*Assistant Examiner*—Sonya Harris-Ogugua
*Attorney, Agent, or Firm*—William H. Drummond; Drummond & Duckworth

[57] ABSTRACT

An illuminated bougie in which the elongate bougie body is formed of flexible light-transmitting material. A socket for detachably attaching the light-transmitting end of a fiber optic bundle is formed in the proximal end of the bougie.

2 Claims, 3 Drawing Sheets

ILLUMINATING BOUGIE AND METHODS FOR DIAGNOSTIC, THERAPEUTIC AND SURGICAL PROCEDURES

This Application is a Continuation Application of U.S. application Ser. No. 08/131,995, filed Oct. 4, 1993, now abandoned which is a Continuation-in-Part of U.S. application Ser. No. 08/073,172, filed Jun. 7, 1993, now abandoned, which was a National Stage Application derived from International Application PCT/US92/07356, filed Aug. 26, 1992, which, in turn, is a Continuation-in-Part of my U.S. application Ser. No. 07/772,332, filed Oct. 7, 1991, now abandoned.

This invention relates to medical devices and methods of use in diagnostic, therapeutic and surgical procedures.

The principal object of the invention is to provide an improved bougie for transmitting light to body tissue.

Another object of the invention is to provide improved diagnostic, therapeutic and surgical procedures which involve use of such a light-transmitting bougie.

These, other and further objects of the invention, will be apparent to those skilled in the art from the following detailed description thereof, taken in conjunction with the drawings in which.

Figure 1:
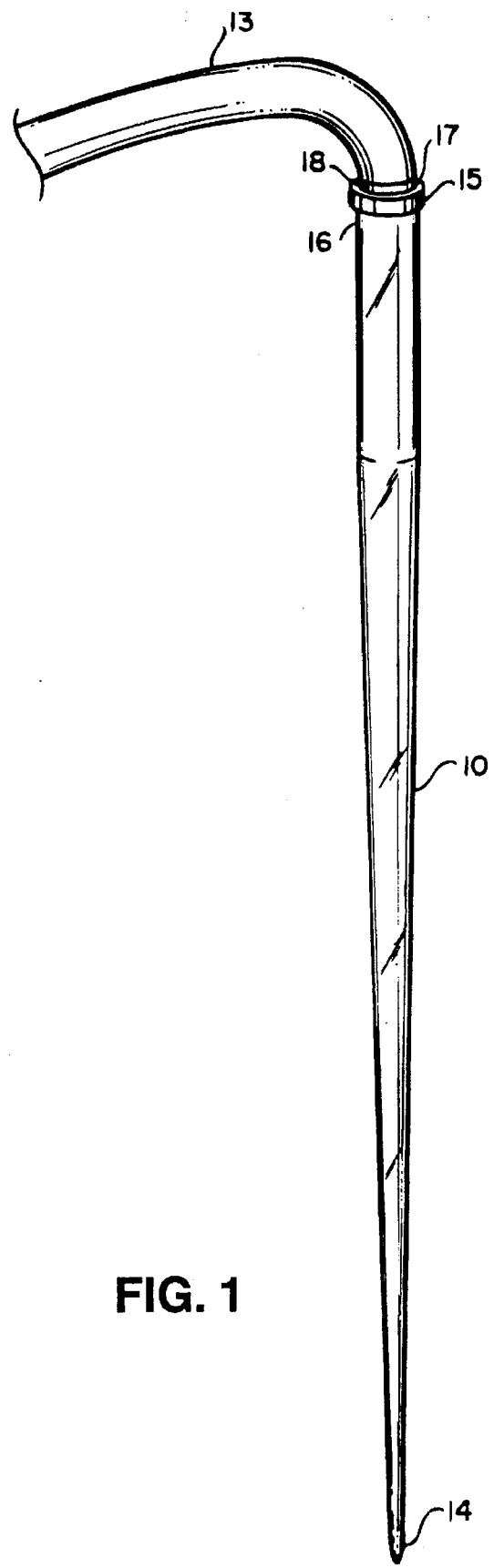
FIG. 1 depicts an illuminated bougie embodying the present invention.

The publication entitled *Laryngoscope*, Volume 96, page 1040 (1986) described a device consisting of a hollow tapered esophageal bougie. An elliptical portal was formed in the distal end of the bougie. A fiber optic bundle, the terminal end of which was cut at a 40° angle, was then inserted into the lumen of the bougie, such that the terminal end of the bundle was then cemented to fix it in the portal. Thus, the bougie described in this article could only transilluminate a very small portion of the esophagus which was directly adjacent the oval portal at the distal end of the bougie. By contrast, as will appear more fully below, the bougie which I have invented can illuminate body tissue along a substantial length corresponding to the length of a major light emitting portion.

Schellenberg, U.S. Pat. No. 1,704,764, disclosed a hollow perforate colonic exploration device formed of translucent rubber, into which a hot-filament electric lamp could be temporarily inserted, to facilitate taking a picture of the walls of the colons and intestines.

Aiken, U.S. Pat. No. 2,797,683, disclosed a rigid bronchoscope formed of a plastic material which transmits light by internal reflection, to be emitted by the leading (distal) tip of the device, in a manner similar to the devices described in the *Laryngoscope* article, cited above.

Briefly, in accordance with my invention, my illuminated bougie comprises an elongate bougie, shaped and dimensioned to be inserted into the body, and having a proximal end and a distal end. The bougie is formed of a flexible light-transmitting material which transmits and diffuses light laterally to illuminate adjacent body tissue along its length. Means are provided for attaching the proximal end of the bougie to the light-transmitting end of a fiber optic bundle.

In accordance with another aspect of the invention, I provide a method of illuminating interior body tissue, which includes the steps of inserting the bougie described above into the body, locating the light-transmitting bougie adjacent selected body tissue to be illuminated, and transmitting light through said bougie to illuminate the selected body tissue.

In a more specific embodiment of the invention, the apparatus and method described above are used to illuminate and/or transilluminate selected body tissue for surgical procedures.

In another embodiment of the invention, the apparatus and method described above are used to illuminate selected body tissue for diagnostic procedures.

In still another embodiment of the invention, the apparatus and method described above are used to illuminate selected body tissue for phototherapy procedures.

According to the broadest aspects of the invention, the bougie is inserted within the body through any normal body opening or, through an incision, into any body cavity, organ or vessel.

The drawings are presented for the purpose of illustrating the practice of my invention, so as to enable those skilled in the art to understand and practice it, but are not invented as limitations upon the scope of the invention. Further, the drawings illustrate the best mode which I presently contemplate for carrying out my invention, again without intending to limit the scope thereof. In these drawings, like reference characters depict the same elements in the several views.

Figure 2:
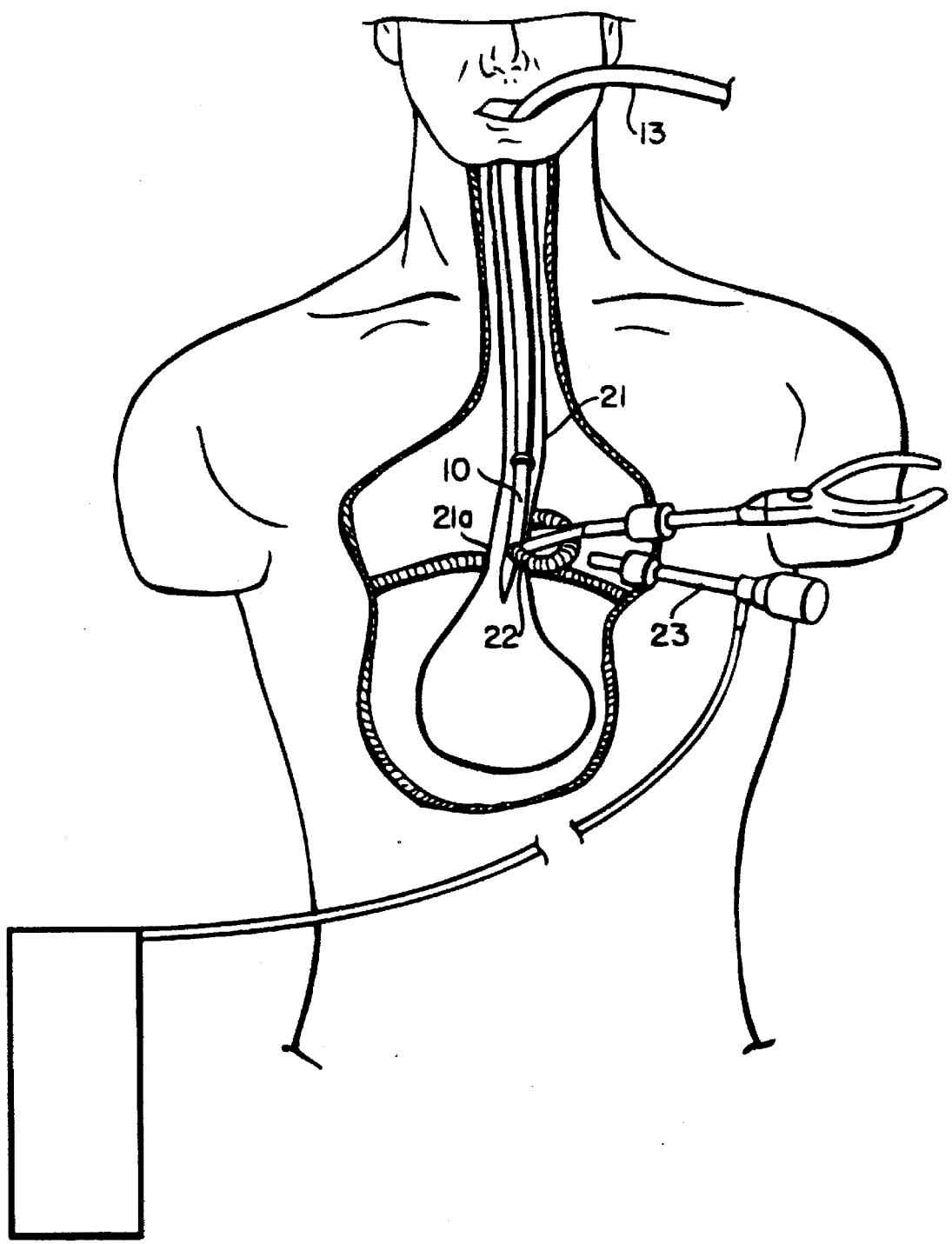
FIG. 2 depicts a procedure for laparoscopic implantation of an anti reflux prosthesis, utilizing the bougie of FIG. 1.

Turning now to the drawings, FIG. 2 depicts a presently preferred embodiment of the invention, consisting of a bougie 10 formed entirely of light-transmitting material. The upper proximal portion A is cylindrically shaped and the remainder is tapered towards the distal end 14. The bougie 10 is imperforate and flexible and is preferably solid. Means are provided, such as a socket 15 formed in the proximal end 16 of the bougie 10 and cooperating collar 18, for attaching the light-transmitting terminal end 17 of a fiber optics bundle 13 to the light-transmitting proximal end of the bougie 10. In the embodiment depicted in FIG. 1, light from the terminal end 17 of the fiber optic bundle 13 is transmitted laterally from the bougie 10 along its entire length for illumination of adjacent tissue.

The shape and dimensions of the bougie can be varied to suit the end use of the device. Thus, for upper laryngeal and esophagus surgery, i.e., Zencker's diverticulum, Barrett's esophagus resections, thoracoscopy, e.g., surgery for ulcer disease, vagotomy for morbid obesity, for reflux esophagitis and for placement of the prosthesis in accordance with my U.S. Pat. No. 5,006,106, the length of the bougie 10 is suitable 20 cm for adults and 15 cm for children. The diameter is suitably 36–40 French for adults and 18–26 French for children. (French size=diameter in mm×3). For insertion into the body through normal body openings, the size of the bougie are adapted for insertion through the opening in question and for location adjacent the selected body tissue to be diagnosed, treated or surgically manipulated. For insertion through an incision into body cavities, organs or vessels, the dimensions of the bougie are selected to suit the requirements of the procedure.

The bougie is used to illuminate or transilluminate organs, cavities and vessels in laparoscopy and regular surgery. The bougie is also used for visualizing parts of the body using the eyes or special photographic equipment, by providing intense light to the outside or from the inside of organs, cavities or vessels.

For diagnostic purposes the bougie is used where the light will show pathology from the inside or outside the body, using intense, continuous or intermittent light bursts, high intensity bulbs or lasers of different colors. For example, very intense light from an esophageal bougie allows the observer the body to see and to circumferentially photograph the chest cavity from outside the body and to arrive at diagnostic conclusions based on light and shadow on lungs, heart, mediastinum and chest wall, without the injurious effects of x-rays.

For phototherapeutic purposes the bougie is used to transmit continuous or intermittent light, regular or laser beams, e.g., for the treatment of tumors which have been sensitized with photosensitizers such as porphyrin derivatives and for killing bacteria which have been stained with a sensitizing dye. Tumors of the skin, oral, anal, rectal and colonic cavities, esophagus, stomach, intestine, liver, pancreas, kidney, bladder, ureter, lung and heart, large and small vessels and even bone can be treated this way, as well as tumors of the brain and spinal column. Small size bougies, even microscopic, can be used to visualize, diagnose and treat small vessels, urethra, ureters, acoustic and respiratory channels using the types of light referred to above.

In the preferred embodiment the bougie 10 is formed of molded silicone plastic or similar flexible plastic having a hardness of approximately 50 durometer (Shore A). Micrometalic particles can be dispersed in the plastic to improve lateral diffusion of the light. Polishing the external surface of the bougie causes light to be transmitted further toward the distal end before it is diffused laterally. However, when body tissue contacts the bougie, the bougie surface-air interface is altered, causing lateral diffusion of the light along the length contacted by the body tissue.

A typical laparoscopic procedure, involving the use of the bougie of my invention is depicted in FIG. 2. The procedure is facilitated by illuminating by the esophagus 21 by means of the bougie 10 which is inserted intra-orally. The wall 21a of the distal esophagus is sufficiently thin to transmit a substantial portion of the light emitted by the bougie 10, facilitating viewing the esophagus and placement of the prosthesis 22, viewing the procedure through a laparoscopic optical viewing device 23.

Figure 3:
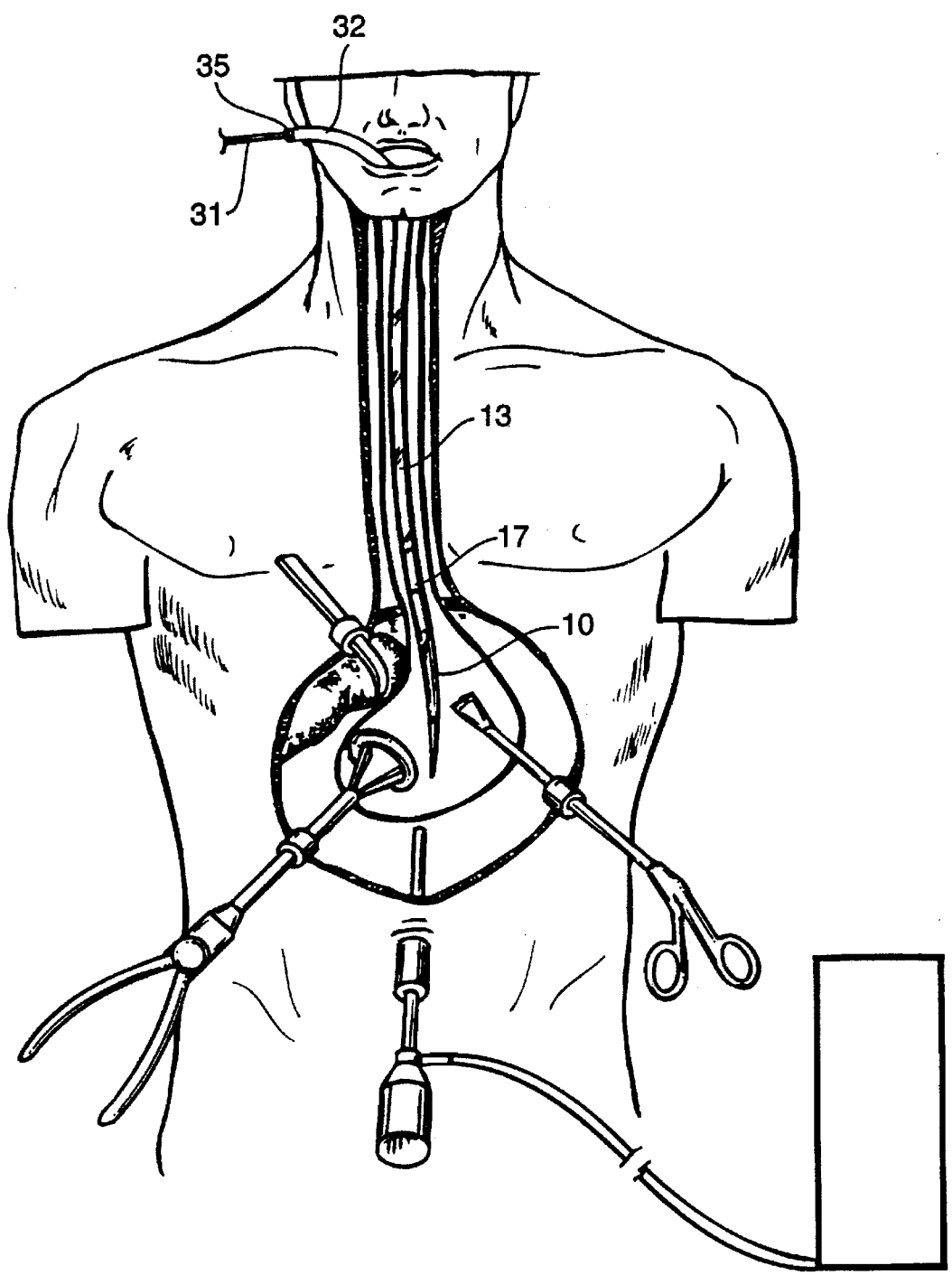
FIG. 3 depicts a laparoscopic abdominal surgical procedure utilizing the bougie of FIG. 1 and further details of the attachment of the bougie to a light source.

As further depicted in FIG. 3, the light-transmitting fiber optics bundle 13, attached at its distal end 17 to the proximal end of the bougie 10, comprises the optical fibers 31, encased in a suitable sheath 32, e.g., silicone plastic. A suitable detachable connection 33 is provided so that the bougie 10 and attached fiber optics bundle 13 can be disconnected form the remote flight source (not shown) for disposal or sterilization and reuse. Since no heat is transmitted from the bougie, it can be left in place during the entire course of a procedure, even several hours, if necessary, without burning the body tissue it contacts, because the light is transmitted to the bougie by a fiber optic bundle from a light source many feet away, rather than from an incandescent filament inside the bougie.

Having now described my invention in such terms as to enable those skilled in the art to understand and practice it without undue experimentation and, having disclosed the best mode I presently contemplate for carrying out my invention, I claim:

1. An illuminated bougie for insertion into a human body through a normal body opening or a surgical incision comprising:

a) an elongate bougie having a proximal end and a distal end, and being formed of a flexible plastic material which transmits and diffuses light laterally to illuminate adjacent body tissue along the entire length of said bougie;

(b) means for attaching the proximal end of said bougie to the light-transmitting end of a fiber optic bundle.

2. A method of illuminating interior body tissue, which includes the steps of:

(a) inserting the bougie of claim 1 into the body;

(b) locating the bougie adjacent selected body tissue to be illuminated; and (c) transmitting light through the entire length of said bougie to illuminate said selected body tissue.

* * * * *